United States Patent [19]
Stanley et al.

[11] Patent Number: 5,632,051
[45] Date of Patent: May 27, 1997

[54] COOLING FLUID CONTAINER

[76] Inventors: Eric D. Stanley; Kirk A. Stanley, both of 3120 Corona Trail Apt. #101, Boulder, Colo. 80301

[21] Appl. No.: 331,183

[22] Filed: Oct. 28, 1994

[51] Int. Cl.$^6$ ..................................... A47G 9/00
[52] U.S. Cl. ...................... 5/636; 5/644; 5/421; 5/925
[58] Field of Search .................. 5/644, 636, 654, 5/420, 421, 919, 925

[56] References Cited

U.S. PATENT DOCUMENTS

| | | | |
|---|---|---|---|
| D. 25,786 | 7/1896 | Stoll . | |
| 2,834,970 | 5/1958 | Nappe | 5/420 |
| 3,864,766 | 2/1975 | Prete, Jr. | 5/644 |
| 3,900,910 | 8/1975 | Nakata | 5/644 |
| 4,411,033 | 10/1983 | Morgan | 5/919 |
| 4,783,866 | 11/1988 | Simmons et al. | 5/644 |
| 4,847,931 | 7/1989 | Bard . | |
| 4,887,326 | 12/1989 | O'Brien et al. . | |
| 4,896,388 | 1/1990 | Bard . | |
| 4,908,893 | 3/1990 | Smit . | |
| 4,942,634 | 7/1990 | Saloff et al. | 5/654 |
| 5,016,303 | 5/1991 | Tanaka et al. | 5/636 |
| 5,173,346 | 12/1992 | Middleotn | 5/420 |
| 5,195,199 | 3/1993 | Sereboff | 5/654 |
| 5,231,720 | 8/1993 | Benoff . | |
| 5,257,429 | 11/1993 | Genis | 5/644 |
| 5,303,435 | 4/1994 | Haar et al. | 5/420 |

*Primary Examiner*—Michael J. Milano
*Attorney, Agent, or Firm*—Lee G. Meyer

[57] ABSTRACT

The invention is a cooling pillow container insert which provides a continuous cool pillow surface and absorbs a pillow user's lost metabolic heat. Preventing thermal discomfort which causes pillow flipping and tossing and turning is the primary goal of the invention. The container slides between a conventional pillow and pillow case. The container is composed of a soft vinyl bag which snugly surrounds a fluid saturated porous foam core. A resealable valve allows fluid to be added or removed at will and the container's temperature to be adjusted. The container promotes heat transfer from the pillow user to the container. The heat is then dispersed uniformly throughout the container's fluid ensuring a uniformly cool pillow surface. Heat is also continuously lost to the surrounding environment. A pillow user's sleep is enhanced in warm temperatures without using an energy source. The container insert can also be used with or without a pillow, as a cooling bed for an animal or a pet.

6 Claims, 3 Drawing Sheets

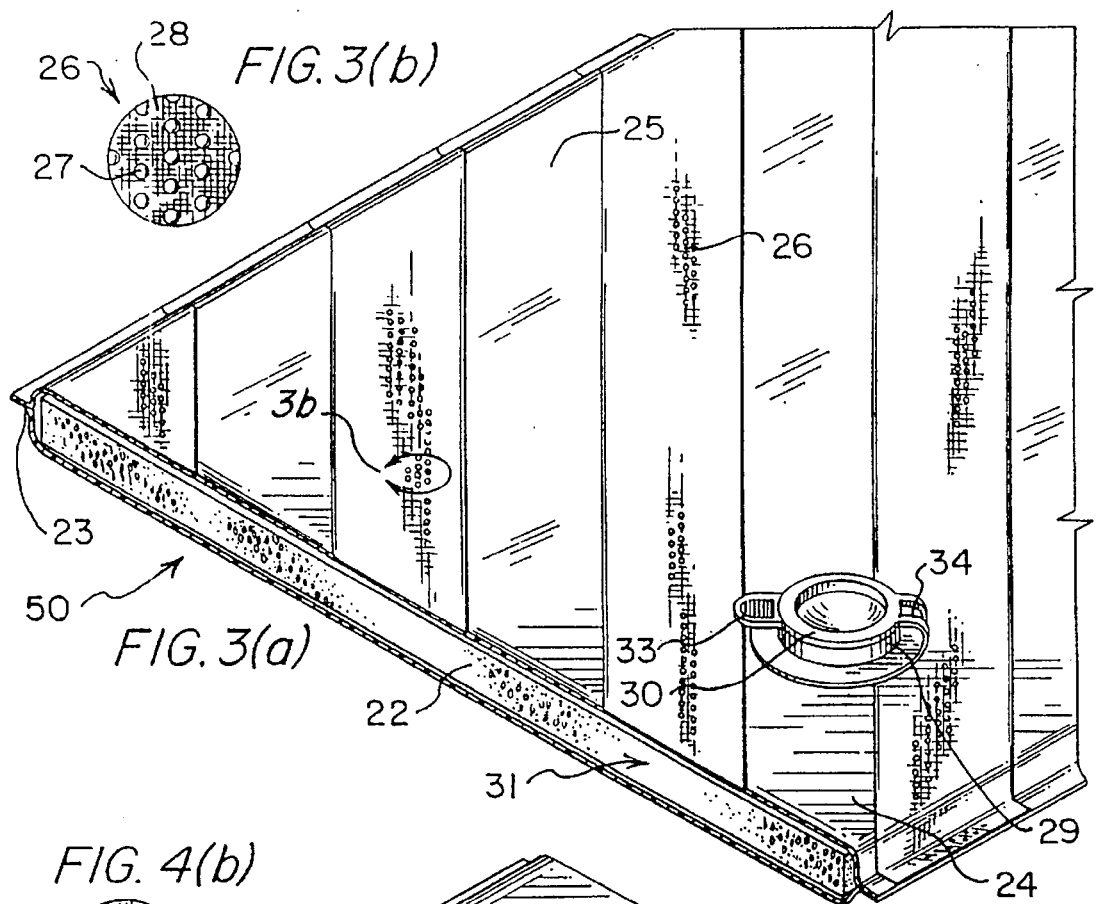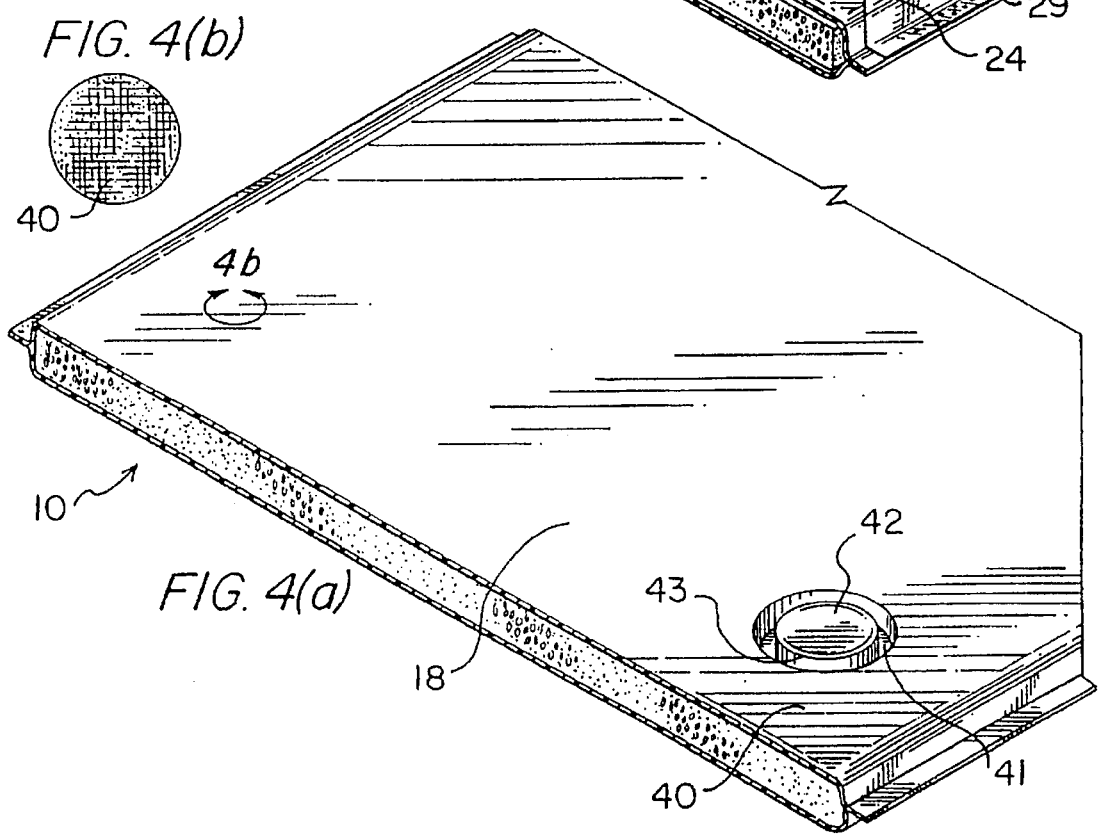

COOLING FLUID CONTAINER

FIELD OF INVENTION

The present invention relates to a fluid filled container which slides between a pillow case and the top of a pillow to provide a constant cool spot for a pillow user. The fluid container pillow insert is ideally suited for enhancing sleep when air temperatures are uncomfortably high and to soothe sunburns, fevers, headaches and the like. The present invention can also be used as a cooling pet bed to make animals and family pets more comfortable.

BACKGROUND OF THE INVENTION

Most people have difficulty sleeping when air temperatures are high. At present, the main solution to this problem is to use powered devices such as air conditioning, fans, etc., to cool air temperatures. Fans and air conditioning require electricity and are noisy.

The present invention solves this problem by using a fluid saturated foam filled container as a pillow insert. While others have designed pillows for various purposes, no one has developed a fluid filled container to conduct a person's or animal's lost body heat away from the body. The following patents are representative of the art.

U.S. Design Pat. No. 25786 (1896) to Stoll discloses a water bag pillow having a large central hole and a tube at each of its four corners. The four tubes serve as both inlets and outlets and are closed by stoppers. The present invention is filled with both foam and fluid and does not possess a large hole or cavity anywhere in its design.

U.S. Pat. No. 4,847,931 (1989) to Bard discloses a pillow with a thin water envelope contained in its bottom half. A dry compressible filler material lies between the pillow's top surface and the water envelope. The present invention does not contain an isolated internal water envelope. Fluid permeates the entire present invention which is placed on top of the pillow, rather than the bottom, so that heat transfer may occur between the insert and the sleeping person.

U.S. Pat. No. 4,896,388 (1990) to Bard discloses an alternative embodiment of U.S. Pat. No. 4,847,931 described above. The alternative embodiment uses a conventional pillow as the compressible filler material between the bottom water envelope and the top surface. The present invention does not contain an isolated fluid envelope, rather, fluid permeates the entire invention. Further, the present invention is placed on top of a pillow so that only a pillow case comes between the invention and the sleeping person.

U.S. Pat. No. 4,887,326 to O'Brien et al. discloses a crescent shaped neck pillow containing dry filling and pockets. The pockets receive gel packs which can be heated or cooled. The present invention is not a neck pillow and is permeated with cooling fluid which is used at room temperature. The fluid does not have to be externally heated or cooled.

U.S. Pat. No. 5,231,720 (1993) to Benoff discloses a pillow having an internal air bag for adjustable firmness. The present invention does not contain an air bag. The present invention is entirely filled with fluid saturated foam.

U.S. Pat. No. 4,908,893 to Smit discloses a beauty pillow with a concave area on its top surface to prevent pillow contact with delicate facial skin. An optional water, air or gel filled bladder can be substituted for conventional pillow stuffing material. The present invention is a fluid and foam filled container that can be inserted between a pillow and case and is not itself a pillow. The present invention does not contain a concave area and is filled with both foam and fluid.

In summary, the present invention overcomes the shortcomings of presently used pillows and powered cooling devices. Powered cooling devices are typically noisy and require electricity. The present invention cools a person noiselessly and without electricity by providing a fluid filled container which slides between the top of a pillow and the pillow case.

The container is entirely filled with a layer of porous foam which is saturated with ordinary tap water. The container temperature is initially lower than body temperature and remains so for several hours. The container cools a person by allowing convective heat exchange between a person's head and the water in the insert. This heat is passively dissipated to the surrounding environment. The water moves freely through the foam, therefore, "hot spots" do not occur and temperature remains uniform throughout the fluid container pillow insert. A pillow, without the present invention, traps body heat causing thermal discomfort and pillow flipping.

Further, the saturated foam prevents water leakage in case of a puncture, prevents noise by preventing waves, minimizing bubbles and acts as a weight sink to maintain the container's proper orientation on a pillow. The container can also be used with or without a pillow as a cooling pet bed to provide cool sleeping and resting conditions for animals and family pets.

SUMMARY OF THE INVENTION

The primary object of the present invention is to provide a pillow insert which creates a pillow surface which is cooler than human body temperature.

Another object of the present invention is to provide a pillow insert that continuously provides comfortably cool sleeping conditions.

Another object of the present invention is to provide a cooling pillow insert which induces sleep.

Another object of the present invention is to provide a cooling pillow insert which enhances sleep.

Another object of the present invention is to provide a pillow insert that provides comfortably cool sleeping conditions without using electricity.

Another object of the present invention is to provide a cooling pillow insert which is filled with fluid saturated foam.

Another object of the present invention is to provide a cooling pillow insert which is filled with a non toxic fluid.

Another object of the present invention is to provide a fluid filled cooling pillow insert which is leak resistant.

Another object of the present invention is to provide a fluid filled cooling pillow insert which is refillable and temperature adjustable.

Another object of the present invention is to provide a pillow insert which cools a person noiselessly.

Another object of the present invention is to provide a cooling pillow insert that is held in the proper orientation by traction, a pillow case, and the weight and uniform fluid distribution within the insert.

Another object of the present invention is to provide a cooling pillow insert which soothes headaches, fevers, sunburns and alcohol hangovers, or anytime a cooling sensation is desired, e.g. after exercise, sunbathing, etc.

Another object of the present invention is to provide a cooling pet bed that continuously provides comfortably cool sleeping and lounging conditions for an animal or pet.

Other objects of this invention will appear from the following description and appended claims, reference being had to the accompanying drawings forming a part of this specification wherein like reference characters designate corresponding parts in the several views.

In the preferred embodiment, a fluid filled container is used as a cooling pillow insert and is placed between a pillow case and a pillow. The insert consists of a vinyl bag snugly surrounding a porous foam core which has been saturated with fluid. Only the pillow case separates the insert from the user's head. The insert temperature is lower than human body temperature. The close contact between the pillow user and the insert, therefore, allows heat to be transferred from the pillow user to the insert by conduction.

The fluid moves freely through the foam core and, therefore, heat is dispersed throughout the pillow insert and passively lost to the surrounding environment, resulting in a uniformly cool surface with no "hot spots". As a result the pillow surface remains uniformly cool. The user is thus afforded a continuous cool spot, which enhances relaxation and sleep.

The saturated foam core further acts to prevent noise by preventing wave action, reduce the possibility of leakage and act as a weight sink to maintain the insert in its proper orientation on the pillow.

The container can also be used with or without a pillow to provide a sleep and relaxation enhancing cool surface for an animal or pet.

BRIEF DESCRIPTION OF THE DRAWINGS

FIG. 3(a) is a top perspective view of the bottom side of an alternative embodiment of the fluid container pillow insert.

FIG. 3(b) is a top plan view of the traction material which is fixed to the bottom side of the alternative embodiment of the fluid container pillow insert.

FIG. 4(a) is a top perspective view of the bottom side of the preferred embodiment of the fluid container pillow insert.

FIG. 4(b) is a top plan view of the flocked vinyl traction material which is fixed to the bottom side of the preferred embodiment of the fluid container pillow insert.

Before explaining the disclosed embodiment of the present invention in detail, it is to be understood that the invention is not limited in its application to the details of the particular arrangement shown, since the invention is capable of other embodiments. Also, the terminology used herein is for the purpose of description and not of limitation.

DESCRIPTION OF THE PREFERRED EMBODIMENT

Figure 1:
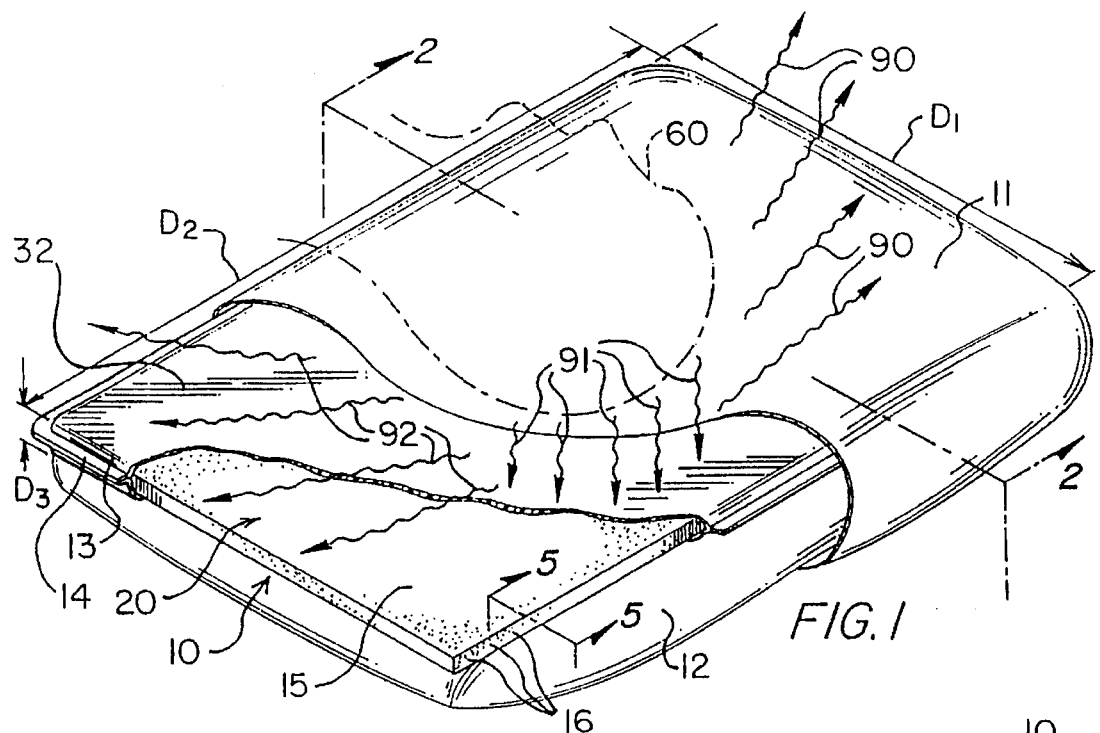
FIG. 1 is a top perspective view of a partial cut-away of the fluid container pillow insert enclosed between a pillow and pillow case.

Referring first to FIG. 1 a top perspective view of a partial cut-away of the fluid container pillow insert 10 enclosed between a pillow 12 and pillow case 11 is shown. The pillow insert consists of a foam core 15 that is saturated with fluid 20 and enclosed in a vinyl bag 13.

In the preferred embodiment of the fluid container pillow insert 10, the foam core 15 is fourteen inches wide d1, twenty-one inches long d2 and one half inch thick d3. A vinyl bag 13 fits snugly around the reticulated foam core 15. These are the approximate dimensions of a conventional bed pillow. These dimensions are substantially larger than a human head (60) and provide enough volume and surface area to dissipate the body heat transferred to the container 10.

The vinyl bag 13 consists of two layers of vinyl which have been sealed together along their perimeters by radio frequency. Flexible vinyl sheets are available in thickness ranging from 2 mm to 100 mm. The preferred embodiment uses 8 mm thick vinyl sheets. The resulting radio frequency seal 14 is water tight and stronger than a heat seal. The top vinyl sheet 32 is noiseless, translucent and soft to the touch.

Figure 5:
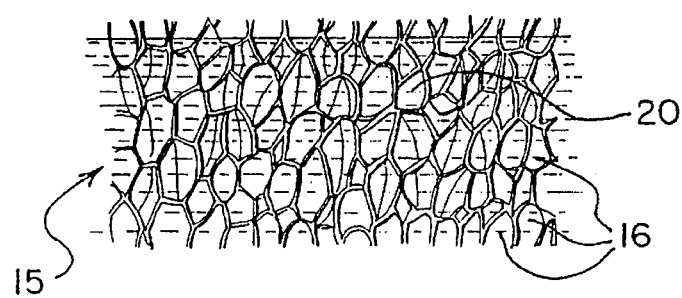
FIG. 5 is a cross-sectional view of the reticulated foam contained in the fluid container pillow insert.

Referring next to FIG. 5 a cross-sectional view of the foam core 15 contained in the fluid container pillow insert 10 is shown. The core 15 consists of reticulated foam composed of polyurethane which is filled with pores 16. The reticulated foam core 15 is saturated with fluid 20. Reticulated foam is processed with an acid treatment of sonic treatment to result in larger pore sizes and is available in pore densities ranging from ten pores per inch (PPI) to sixty PPI. The preferred embodiment of the pillow insert 10 uses a foam core 15 with a pore density of twenty PPI. At a pore density of twenty PPI, essentially all of the fluid 20 contained in the fluid container pillow insert 10 is retained in the foam core 15. This reduces both noise and the risk of leakage if the container 10 is punctured or torn. Noise is reduced because fluid 20 is retained in the foam core 15 and not free to audibly slosh or splash. Risk of leakage is reduced because fluid is retained in the reticulated foam and not free to leak out of a puncture or a cut. The foam core 15 will not release the fluid 20 to result in leakage unless pressure is applied at or near a puncture or cut. Additionally, because all the fluid is evenly distributed throughout the core 15, the fluid 20 does not pool in one spot. This allows the core 15 to act as a weight sink which holds the invention in place and prevents the invention from slipping out of place.

The fluid 20 used in the preferred insert embodiment 10 is water. Water is non toxic and readily available to fill the insert 10.

Figure 2:
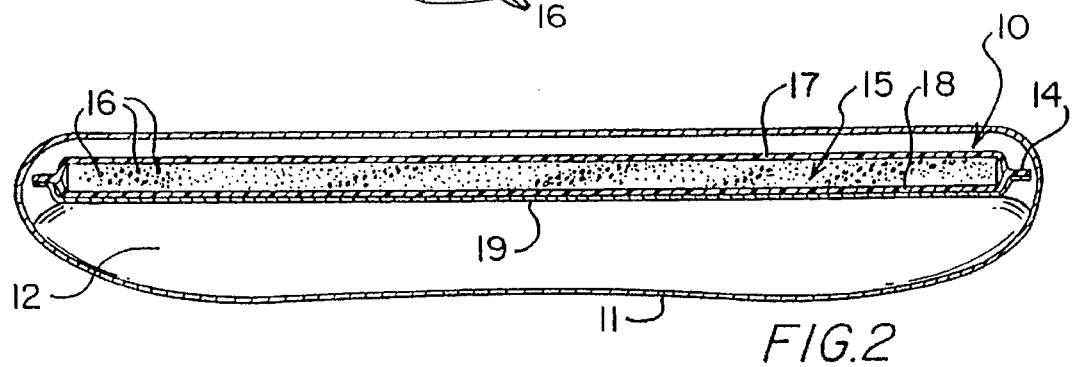
FIG. 2 is a front cross-sectional view of the fluid container pillow insert enclosed between a pillow case and pillow.

Referring next to FIG. 2 a front cross-sectional view of the fluid container pillow insert 10 enclosed between a pillow 12 and a pillow case 11 is shown. The container 10 consists of a top vinyl sheet 17 and bottom vinyl sheet 18 which are radio frequency sealed 14 to enclose a reticulated foam insert 15.

A backing 19 is fixed to the bottom vinyl sheet 18. The container 10 is placed on a conventional pillow with the backing 19 contacting the pillow 12 and the top vinyl sheet 17 facing up.

Referring again to FIG. 1 the only layer between the fluid container pillow insert 10 and a person's head 60, is the pillow case 11. This close contact allows a user's body heat to be absorbed by the insert (10) and conducted throughout the fluid 20 and finally passively transferred to the surrounding environment as indicated by arrows 91. The fluid 20 disperses body heat from the point where the head contacts the pillow and diffuses the heat throughout the fluid container pillow insert 10 as indicated by arrows 92.

The fluid temperature may initially be at room temperature which is lower than human body temperature and remains so for hours. A user may also adjust the initial temperature of the fluid 20 by filling the container 10 with a fluid 20 at the desired temperature. By dispersing a person's body heat throughout the fluid container pillow insert 10, the pillow surface remains uniformly cool providing a person with a constant cool surface to sleep on. The fluid container pillow insert 10 warms slight during use, and therefore does not overcool a sleeping user. If a container user desires an initial temperature lower than room temperature, the user can fill the container with colder water.

Heat transfer to the pillow insert 10 helps to enhance sleeping comfort by conducting heat away from a person's head 60. Over 50% of a person's body heat is lost through the head 60. The container 10, therefore enhances the overall comfort of the user by conducting lost body heat away from the user.

A pillow case 11 fits securely around the insert 10 and a conventional pillow 12. The combination of the traction backing 19, the snug pillow case 11 and the weight of the insert 10, securely holds the container 10 flat against the pillow 12.

Referring next to FIG. 3(a) a top perspective view of the bottom side of an alternative embodiment of the fluid container pillow insert 50 is shown. The alternative embodiment of the container 50 consists of a reticulated foam core 22 which is saturated with fluid 31, preferably water, and snugly enclosed by a 8 millimeter thick vinyl bag 24. The vinyl bag 24 consists of two vinyl sheets fused together around their perimeters by a radio frequency seal 23.

In the alternative embodiment 50, a simple fluid inlet 29 is attached to the bottom 25 of the vinyl bag 24. The inlet 29 is a plastic tube which is easily opened and closed by a pop cap 30 using a pull tab 33. The pop cap 30 is attached to the inlet by thin plastic strips 34 to prevent the loss of the pop cap 30.

Strips of traction material 26 are attached to the bottom 25 of the vinyl bag 24 to help maintain the container 50 properly oriented flat against a pillow.

Referring next to FIG. 3(b) a top plan view of the traction material 26 which is fixed to the bottom side of the alternative embodiment of the pillow insert 50 is shown. JIFFY GRIP brand traction material 26 is used in the alternative insert embodiment 50. JIFFY GRIP consists of cloth 28 studded with raised vinyl dots 27. The JIFFY GRIP traction material 26 contacts the top of a pillow and keeps the insert 50 from slipping out of position. Similar traction material with rubber dots is also available from other manufacturers. The JIFFY GRIP combined with the weight of the insert 50 and the tension of the pillow case, keeps the insert 50 properly oriented on the pillow. Additionally, because the fluid 31 is uniformly distributed throughout the foam core 22, the fluid 31 does not pool. The container 50, therefore, acts as a weight sink and is not pulled out of orientation by pooled fluid 31.

Referring next to FIG. 4(a) a top perspective view of the bottom side of the preferred embodiment of the fluid container pillow insert 10 is shown. In the preferred embodiment, a recessed finger-well style valve 43 is inserted through the bottom vinyl sheet 18 of the container 10. The seal 41 between the valve 43 and the bottom vinyl sheet 18 is water tight. The valve 43 is one half to one inch in diameter and is sealed by a threaded screw cap 42. The cap 42 is unscrewed when fluid is added to or removed from the insert 10. The bottom sheet 18 also comprises a traction material 40.

Referring next to FIG. 4(b) a top plan view of the traction material 40 which is fixed to the bottom vinyl sheet 18 of the preferred pillow insert embodiment 10 is shown. The traction material 40 is composed of flocked vinyl. The traction material 40 contacts the top surface of a pillow 12 and prevents the container 10 from slipping out of position. The combination of the flocked vinyl 40 bottom sheet 18, the weight of the container 10, the lack of fluid 20 pooling and the tension of the pillow case 11, keeps the container 10 in the proper orientation on the pillow 12.

Figure 6:
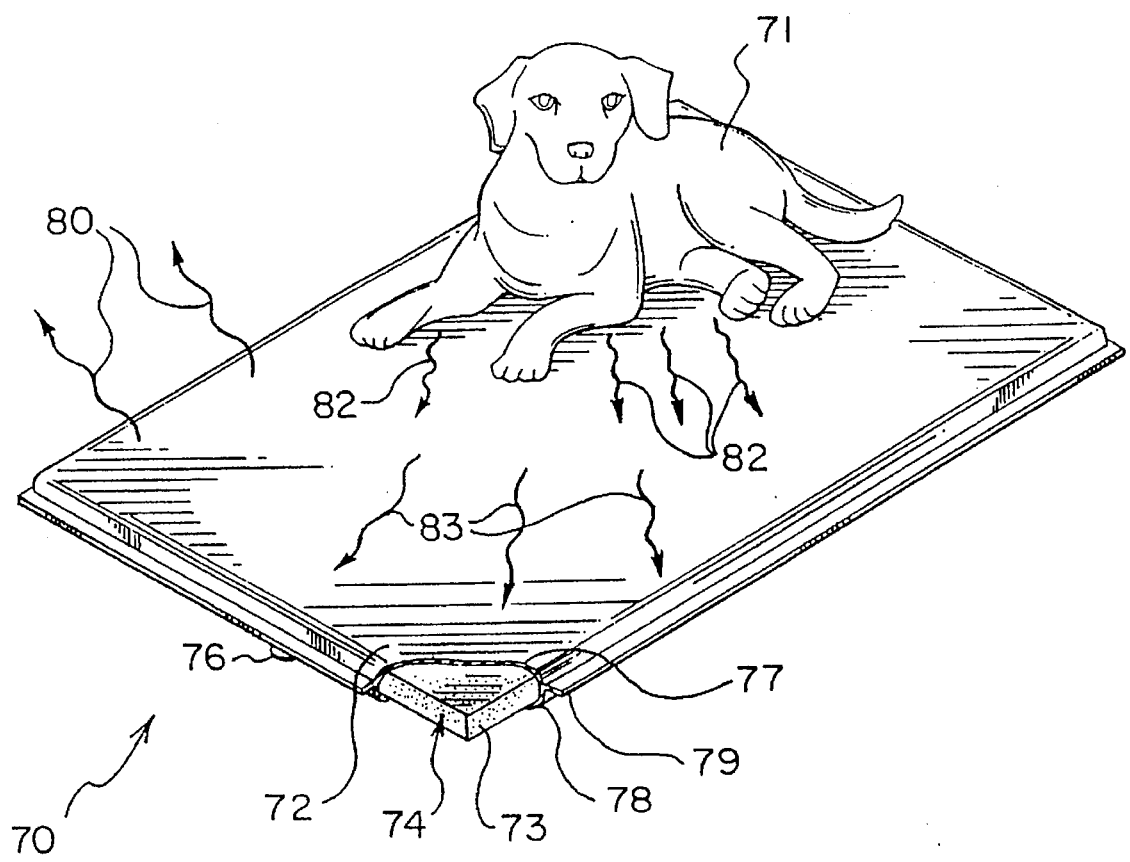
FIG. 6 is a top perspective view of a partial cut-away of an alternative embodiment of the fluid container being used as a cooling pet bed.

Referring next to FIG. 6 a top perspective view of a partial cutaway of an alternative embodiment 70 of the insert being used as a pet bed is shown. The pet bed embodiment 70 of the present invention is substantially similar to the other two embodiments 10, 50.

The pet bed embodiment consists of a foam core 73 which may or may not be reticulated foam. The foam core 73 is saturated with fluid 74 and snugly enclosed by a vinyl bag 72. The vinyl bag is composed of an upper 77 and lower vinyl sheet 78 fused together with a strong water tight radio frequency seal 79. The flexible vinyl sheets are available in thicknesses that range from 2 millimeters to 100 millimeters. 20 millimeter thick vinyl sheets are used in the pet bed embodiment to help prevent an animal's claws from tearing or puncturing the insert 70. The pet bed embodiment 70 has a simple fluid inlet and outlet 76 attached in a water tight fashion to its lower vinyl sheet 78. The pet bed embodiment saturates the reticulated foam core 73 with water as the preferred fluid 74.

The pet bed embodiment has a dimension substantially larger than the body size of the pet 71 or animal. The pet bed embodiment should be twice the size of the pet's body size in order to provide enough volume and surface area to dissipate the pet's 71 body heat.

The pet bed embodiment 70 will be at room temperature unless used in the prior few hours. The pet bed 70 can be made cooler by adding cooler fluid 74 to the bed (70). The pet's 71 body heat is transferred to the fluid 74 in the present invention 70 as indicated by arrows 82. The heat is then dispersed throughout the fluid 74 of the pet bed 70 as indicated by arrows 83 and passively transferred to the surrounding environment as indicated by arrows 80.

Although the present invention has been described with reference to preferred embodiments, numerous modifications and variations can be made and still the result will come within the scope of the invention. No limitation with respect to the specific embodiments disclosed herein is intended or should be inferred.

I claim:

1. In combination with a conventional pillow and a pillow case covering said conventional pillow, a cooling fluid container, comprising:
    an outer membrane having an outer dimension surrounding an inner foam core;
    said inner foam core having a dimension substantially similar to said outer dimension of said outer membrane;
    a fluid permeating said inner foam core;
    wherein said fluid container is located between said pillow and said pillow case and wherein said fluid container further comprises a lower nonsliding surface functioning to stick to a top plane of the conventional pillow.

2. The cooling fluid container of claim 1, wherein:

said lower nonsliding surface of said fluid container further comprises a resealable fluid inlet and outlet valve.

3. The cooling fluid container of claim 2, wherein:

said lower nonsliding surface further comprises a studded cloth; and said studded cloth is chosen from a group of vinyl studded and rubber studded cloth.

4. The cooling fluid container of claim 2, wherein:

said lower nonsliding surface further comprises a flocked vinyl.

5. The cooling fluid container of claim 2, wherein:

said inner foam core further comprises reticulated polyurethane foam; and said inner foam core further comprises a porosity ranging from 10 pores per inch to 60 pores per inch.

6. In combination with a conventional pillow and pillow case covering said conventional pillow a cooling fluid container comprising:

an outer membrane having an outer dimension surrounding an inner foam core and having a resealable fluid inlet and outlet valve;

a fluid permeating said inner foam core;

said inner foam core having a dimension substantially similar to said outer dimension of said outer membrane and further comprising reticulated polyurethane foam having a porosity ranging from 10 pores per inch to 60 pores per inch; and said outer membrane having a lower non-sliding surface functioning to stick to a top plane of a conventional pillow comprising a rubber studded cloth or flocked vinyl.

* * * * *